United States Patent [19]

Annen et al.

[11] Patent Number: 4,670,427
[45] Date of Patent: Jun. 2, 1987

[54] 1α,2α-METHYLENE-6-METHYLENE- AND 6α-METHYLPREGNENES, THEIR PREPARATION AND PHARMACEUTICAL USE

[75] Inventors: Klaus Annen, Münster-Albachten; Henry Laurent, Berlin; Walter Elger, Berlin; Rudolf Wiechert, Berlin; Helmut Hofmeister, Berlin; Michael Töpert, Berlin, all of Fed. Rep. of Germany

[73] Assignee: Schering Aktiengesellschaft, Berlin and Bergkamen, Fed. Rep. of Germany

[21] Appl. No.: 692,488

[22] Filed: Jan. 18, 1985

[30] Foreign Application Priority Data

Jan. 20, 1984 [DE] Fed. Rep. of Germany ....... 3402330

[51] Int. Cl.⁴ .......................... C07J 1/00; A61K 31/56
[52] U.S. Cl. ................................. 514/178; 260/397.4; 260/397.45
[58] Field of Search .................. 260/397.4, 397.45; 514/178

[56] References Cited

U.S. PATENT DOCUMENTS 3,366,653 1/1968 Wiechert et al. ............... 260/397.4

FOREIGN PATENT DOCUMENTS 957222 5/1964 United Kingdom ........... 260/397.45

OTHER PUBLICATIONS

Chemical Abstracts (1973) 78 Par. 4423y.

Primary Examiner—Leonard Schenkman
Assistant Examiner—Joseph A. Lipovsky
Attorney, Agent, or Firm—Millen & White

[57] ABSTRACT

1α,2α-methylene-6-methylene- and 6α-methylpregnenes of Formula I

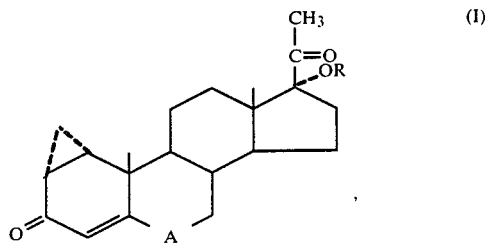

wherein
A is

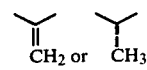

and
R is a hydrogen atom, an acyl group, or an alkoxymethyl group
are strong antiandrogens, and suitable for the topical treatment of seborrhea, acne, alopecia, and hirsutism.

10 Claims, No Drawings

1α,2α-METHYLENE-6-METHYLENE- AND 6α-METHYLPREGNENES, THEIR PREPARATION AND PHARMACEUTICAL USE

BACKGROUND OF THE INVENTION

The present invention relates to 1α, 2α-methylene-6-methylene- and 6α-methylpregnenes, processes for the production thereof, and pharmaceutical preparations containing them.

Cyproterone acetate (17-acetoxy-6-chloro-1α,2α-methylene-4-pregnene-3,20-dione), described by Wiechert, Neumann et al. (Arzneimittelforschung 17 [1967] 1103, and U.S. Pat. No. 3,423,507, has thus far been the most effective antiandrogen with ovulation-inhibiting (antigonadotropic) activity. It extensively hampers the influence of androgens on their target organs by competitive inhibition. Thus, cyproterone acetate lessens sexual drive in men with sexual deviations and, in the final analysis, represents a medicinial alternative for castration for criminological considerations.

Treatment with cyproterone acetate is of special significance for prostate carcinoma and prostate hypertrophy. It is generally known that androgens convey growth-promoting impetus to the carcinoma of the prostate—just as to the tissue, on the substrate of which it develops. By eliminating the androgen effect with the aid of antiandrogens, the growth of the carcinoma can be inhibited.

The antiandrogenic activity of cyproterone acetate makes it possible to effect specific therapy of androgenization phenomena in females: Favorable effects can be exerted on pathological hairiness in hirsutism, androgenetic alopecia, as well as increased function of the sebaceous glands in case of acne and seborrhea ("Ärztliche Praxis" [Medical Practice] 100:3461 [1978]).

Cyproterone acetate was synthesized within the scope of a synthesis program for oral gestagens. The compound shows strong progestational as well as antigonadotropic activities. The strongly progestational activity was demonstrated in the Clauberg test on rabbits, and the antigonadotropic effect was proven in the ovulation inhibiting test on rats.

A combination of cyproterone acetate (gestagen) and ethynylestradiol (estrogen) is available as a preparation for the treatment of androgenization symptoms in women and, at the same time, as a reliable contraceptive for those women who suffer primarly from these symptoms or who develop or show aggravation of acne and similar symptoms when using other ovulation-inhibiting agents.

In all these cases, cyproterone acetate is used systemically. In contrast, topical use of cyproterone acetate does not lead to any substantial success.

It would be desirable to have an agent capable of such topical administration for such uses.

SUMMARY OF THE INVENTION

It is an object of this invention to provide such an agent having valuable pharmacological properties.

Upon further study of the specification and appended claims, further objects and advantages of this invention will become apparent to those skilled in the art.

These objects have been achieved by providing 1α,-2α-Methylene-6-methylene- and 6α-methyl-pregnenes of Formula I

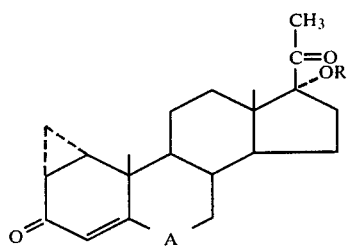

wherein
A is

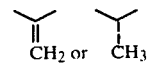

and
R is a hydrogen atom, an acyl group, or an alkoxymethyl group.

DETAILED DISCUSSION

The 6α-methylpregnenes of Formula I are pharmacologically active compounds. They show antiondragenic activity, e.g. topically, e.g., they inhibit lipogenesis of sebaceous glands upon epidermal application and show an only weak effect in the antiandrogen test upon subcutaneous and oral adminstrations. They furthermore exhibit strong ovulation-inhibiting and weak gestagen activity.

The 6-methylene compounds of Formula I, from which the 6α-methyl compounds can be prepared, also show such antiandrogenic activity, but do not exhibit an ovulation-inhibiting effectiveness, or show this effectiveness to an only minor extent.

In the free 17-hydroxy compounds of Formula I, the gestagen properties are further diminished whereas the antiandrogenic characteristics still continue to exist.

The novel compounds of Formula I are of great interest on account of their antiandrogenic activity which, in some compounds, is coupled with ovulation-inhibiting effect (the 6α-methyl compounds). They are all suitable, in particular, for the topical treatment of seborrhea, acne, alopecia, and hirsutism.

The pharmacological activity spectrum of the compounds of this invention was examined, using as an indicative example 17α-acetoxy-6α-methyl-1α,2α-methylene-4-pregnene-3,20-dione as compared with cyproterone acetate.

In order to determine the systemic antiandrogenic activity, inhibition of the increase in weight of seminal vesicle and prostate, caused by testosterone propionate, was investigated upon subcutaneous and oral administration in rats.

In the ovulation-inhibition test on rats, the test compounds were administered subcutaneously or orally over 4 days and, by tubal inspection, the percentage of animals was determined that showed inhibition of ovulation.

The results of the gestagen effect were obtained in the Clauberg test upon subcutaneous administration of the active compounds to castrated female rabbits. In the histological sections, the secretory conversion of the endometrium was determined. The McPhail scale was utilized for this determination (evaluation grades 1–4; 1=no conversion; 4=complete conversion).

The effect of the test compounds on lipogenesis is determined as follows:

Male, fertile hamsters weighing about 100–120 g are castrated and substituted subcutaneously with daily 0.1 mg of testosterone propionate. The right ear of each test animal is treated twice daily for three weeks with respectively 0.01 ml of a 1% strength solution of the test compound in acetone (or, in the control group, only with 0.01 ml of solvent). Then the animals are sacrificed and in each case a defined tissue area 8 mm in diameter is punched out from the treated right ear as well as the untreated left ear. The ventral and dorsal sides of the punched-out areas are separated from each other along the ear cartilage, immediately transferred into Dulbecco's modification of Eagle's medium, to which has been added 4 mmol of glutamine and 10% calf serum and which contains, to avoid microbial contamination, 100 IU/ml of penicillin, 100 μg/ml of streptomycin, 125 μg/ml of kanamycin, 25 IU/ml of nystatin, and 10 μg/ml of gentamycin, and incubated for one hour at 37° C.

Then the punched-out portions are transferred, under sterile conditions, into fresh culture medium containing 1 μCi/ml $C^{14}$ tagged sodium acetate and incubated for 4 hours at 37° C. Subsequently, the specimens are introduced into 2 ml of a proteolysis solution of 0.05 mole of tris buffer, pH=7.5, 0.01 mole of disodium ethylenediaminetetraacetic acid, 0.5% of sodium dodecyl sulfate, and 0.1% of proteinase K (company: E. Merck AG, Darmstadt, Federal Republic of Germany), and incubated for 24 hours at 37° C.

The thus-obtained specimens are extracted once with 5 ml of chloroform and once again with 3 ml of chloroform; the combined chloroform extracts are concentrated under vacuum, and their content of radiolabeled lipids is determined in a scintillation counter.

The percentage inhibition of lipogenesis of the treated control group is calculated by comparison with the control group treated only with solvent.

The table below shows the results obtained in these tests.

| | Antiandrogen Test | | | | | |
|---|---|---|---|---|---|---|
| | | s.c. | | | p.o | |
| Compound | Dose [mg] | Sem. Ves.* [mg] | Prostate* [mg] | Dose [mg] | Sem. Ves.* [mg] | Prostate* [mg] |
| 17α-Acetoxy-6α-methyl- | 1.0 | 26 | 20 | 3.0 | 36 | 33 |
| 1α,2α-methylene-4-pregnene- | 0.3 | 27 | 20 | 1.0 | 44 | 39 |
| 3,20-dione (According | 0.1 | 33 | 29 | 0.3 | 57 | 43 |
| to Invention) | 0.03 | 27 | 19 | 0.1 | 57 | 48 |
| 17α-Acetoxy-6-chloro-1α,2α- | 3.0 | 7 | 8 | 10.0 | 9 | 11 |
| methylene-4,6-pregnadiene- | 1.0 | 12 | 13 | 3.0 | 14 | 13 |
| 3,20-dione (Cyproterone | 0.3 | 16 | 14 | 1.0 | 18 | 14 |
| Acetate as Comparison) | 0.1 | 29 | 25 | 0.3 | 38 | 29 |
| Control, Castrated | | 6 | 7 | | 5 | 7 |
| Control, Castrated + 0.1 mg Testosterone Propionate | | 37 | 32 | | 52 | 45 |

| | Ovulation Inhibition Test | | | | Clauberg Test | | Lipogenesis Test | | | |
|---|---|---|---|---|---|---|---|---|---|---|
| | s.c. | | p.o | | s.c. | | Right Ear | | Left Ear | |
| Compound | Dose [mg] | Inhibition % | Dose [mg] | Inhibition % | Dose [mg] | McPhail Value | Conc. % | Inhib. % | Conc. % | Inhib. % |
| 17α-Acetoxy-6α- | 1.0 | 100 | 1.0 | 100 | 0.03 | 1.6 | 1.0 | 66 | 1.0 | 22 |
| methyl-1α,2α- | 0.3 | 83 | 0.3 | 100 | 0.01 | 1.5 | 0.3 | 40 | 0.3 | 5 |
| methylene-4- | 0.1 | 33 | 0.1 | 0 | 0.003 | 1.3 | 0.1 | 48 | 0.1 | 11 |
| pregnene-3,20-dione (Acc. to Invention) | | | | | 0.001 | 1.3 | 0.03 | 26 | 0.03 | 9 |
| 17α-Acetoxy-6- | 3.0 | 100 | 3.0 | 100 | 0.1 | 2.9 | 1.0 | 29 | 1.0 | 28 |
| chloro-1α,2α- | 1.0 | 60 | 1.0 | 100 | 0.03 | 2.7 | | | | |
| methylene-4,6- | 0.3 | 16 | 0.3 | 0 | 0.01 | 2.3 | | | | |
| pregnadiene-3,20-dione (Cyproterone Acetate as Comparison) | | | | | 0.003 | 1.6 | | | | |
| Control, Castrated | | | | | | | 62 | 61. | | |
| Control, Castrated + 0.1 mg. Testosterone Propionate | | | | | | | 0 | 12 | | |

*Organ weight per 100 g body weight

In the antiandrogen test on rats, the 6α-methyl compound of this invention shows, upon subcutaneous and oral administration, a significantly weaker efficacy than cyproterone acetate. In the ovulation inhibition test on rats, the compound of this invention shows three times the efficacy of cyproterone acetate.

In the subcutaneous Clauberg test on rabbits, the 6α-methyl compound shows only marginal effectiveness and has a substantially weaker activity than cyproterone acetate.

Surprisingly, the 6α-methyl compound of this invention inhibits, when applied epidermally, the lipogenesis of sebaceous glands in the hamster ear. The effect of testosterone propionate on the stimulation of lipogensis in castrated animals is in this case neutralized in dependence on the dosage. In the maximum dose of 1%, the inhibition of lipogensis by the compound of this invention is just as strongly pronounced as in the castrated control without the administration of testosterone propionate, i.e. the effect of testosterone is fully inhibited.

The 6α-methyl compounds of Formula I are preferred. In the 6-methylene compounds of Formula I, the favorable properties of the 6α-methyl compounds, obtainable therefrom, are not as yet so strongly pronounced.

Based on the strong inhibition of lipogenesis upon epidermal application and on the low antiandrogenic effect upon subcutaneous and oral administration, all of the compounds of this invention and the 6α-methyl compounds of Formula I, in particular, can be utilized, in mammals, including humans, particularly females, as antiandrogens for the topical treatment of seborrhea, acne, alopecia, and hirsutism.

The 6αmethyl comounds can also be systemically administered for purposes of ovulation inhibition, e.g., analogously to ihe known agent cyproterone acetate. Unlike cyproterone acetate, such an administration will not concurrently achieve an antiandrogenic effect, as described above. This can be advantageous where only the ovulation inhibition effect is desired.

The topical preparations can be produced in the usual way by converting the active agents with suitable excipients into the desired forms of administration, such as, for example, solutions, gels, lotions, creams, ointments, powders, or plasters.

The antiandrogen is present in the pharmaceutical preparations preferably in a concentration of about 0.05-5.0% by weight. They are used analogously to other topical preparations, e.g., Topterone (U.S. Pat. No. 4,039,669) by administration to the affected area several times, e.g., 1-3 times per day.

Suitable excipients for solutions and gels are, for example, water, ethanol, propanol, glycerol, methylcellulose, hydroxypropylcellulose, carboxypolymethylene, etc.

The lotions or creams (oil/water emulsions) and the ointments (water/oil emulsions) can be manufactured by the conventional methods, using conventional emulsifiers (*Kirk-Othmer: Encyclopedia of Chemical Technology*, 3rd ed., 1979; John Wiley and Sons, New York, 8:900–930; and *Dr. Otto-Albrecht Neumulluer: Rompps Chemie Lexikon*, 7th ed., 1973, Franckh'sche Verlagshandlung stuttgart, pp. 1009–1013). The waxes, emulsifiers, and other additives used for these emulsions are the same as used conventionally (*Dr. Otto-Albrecht Neumuller: Rompps Chemie Lexikon*, 7th ed., 1973, Franckh'sche Verlagshandlung Stuttgart, pp. 147 and 1428).

The topical preparations of this invention in the form of an oil/water emulsion can consist of hydrophilic and/or lipophilic active ingredients, lipid phase, oil/water emulsifier, aqueous phase, and preservative. Suitable as the hydrophilic and/or lipophilic additives are moisturizing factors (hydrocomplexes), e.g., glycerol, polyethylene glycols, or amino acid mixtures, "Puroba" oil (=jojoba oil), vitamins (preferably vitamins A and E), vitalizing complexes (e.g. placenta extracts), enzymes, herbal extracts (e.g. hamamelis extract or camomile extract) or proteins (e.g. collagen). Suitable as the oily phase or as the lipid phase in the oil/water emulsion are hydrocarbons, e.g. "Vaseline", paraffins, or stearin, or waxes, e.g. beeswax. Suitable oil/water emulsifiers are, for example, stearyl alcohol, polyoxyethylene stearates (e.g., "Myrj"), complex emulsifiers (e.g. "Amphoterin"), and sorbitan fatty acid esters (e.g. "Span") or carboxyvinyl polymers (e.g. "Carbopol"). The aqueous phase can additionally contain buffer compounds, such as, for example, the disodium salt of ethylenediamine-N,N,N',N'-tetraacetic acid, and preservatives, such as chlorquialdol, parabens, or benzalkonium chloride.

In the oil/water emulsion, the proportion of the internal emulsion is preferably 10-49% by weight; the particle size of the internal emulsion ranges preferably between 1 μm and 100 μm.

The topical preparation of this invention in the form of a water/oil emulsion likewise consists of hydrophilic and/or lipophilic additives, such as they are also utilized in the oil/water emulsion, lipid phase, water/oil emulsifier, and aqueous phase. A suitable oily phase or fatty phase of the water/oil emulsion is constituted by hydrocarbons, e.g., paraffins and "Vaseline", synthetic, vegetable, and animal oils or waxes (e.g., olive oil, peanut oil, fine bone oil, almond oil, lanolin, beeswax, or sunflower oil); a suitable aqueous phase is purified demineralized water, and usable as the water/oil emulsifier is wool fat (=lanolin), fatty alcohols, e.g. cetyl alcohol, myristyl alcohol, stearyl alcohol, or ceryl alcohol, fatty acid esters, e.g. beeswax (cera alba) or wax alcohol esters or mixed esters (e.g. "Dehymuls").

In the water/oil emulsion, the proportion of the internal emulsion is preferably 30-49% by weight; the particle size of the internal emulsion ranges preferably between 1 μm and 100 μm.

The finely dispersed system is additionally combined with the micronized active agent (particle size preferably 1-20 μm) and optionally also with fragrances, e.g. those of the "Crematest" series, and stirred until uniform distribution is achieved.

The compounds of Formula I according to this invention possess in the 17α-position of the steroid skeleton a hydroxy, acyloxy, or alkoxymethoxy group (OR).

Acyloxy is understood to include acid residues derived from acids usually employed in steroid chemistry for esterifications. Preferred acids are hydrocarbon aliphatic or aromatic carboxylic acids of 1-7 carbon atoms, e.g. monocarboxylic acids, such as acetic acid, propionic acid, butyric acid, caproic acid, enanthic acid, and benzoic acid, and dicarboxylic acids, such as succinic acid and adipic acid.

Alkoxy is understood to include preferably methoxy, ethoxy, and propoxy in the alkoxymethyl group and generally is of 1-3 C-atoms.

The compounds of this invention according to Formula I can be prepared by conventionally treating 1α-chloromethyl-6-methylene-pregnenes of Formula II

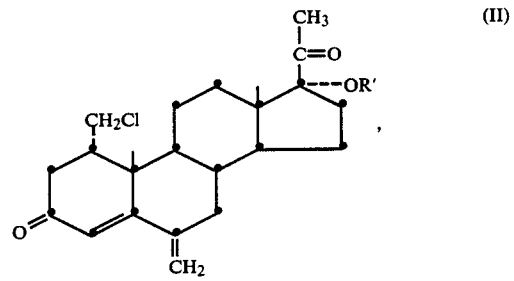

(II)

wherein R' is an acyl or alkoxymethyl group, with a base, thus forming the 1,2-methylene ring by splitting off HCl, and optionally thereafter conventionally converting the 6-methylene compound into the 6α-methyl compound by catalytic hydrogen transfer reaction and acidic working-up process, or conventionally performing in one step the HCl cleavage to the 1,2-methylene compound and the hydrogenation to the 6α-methyl compound under the conditions of catalytic hydrogen transfer reaction with an acidic working-up step, and optionally subsequently hydrolyzing a 17α-acyloxy group.

Ring closure of the 1α-chloromethyl group, splitting off HCl, to the 1α,2α-methylene group takes place with strong bases. Suitable bases include inorganic bases, such as sodium or potassium hydroxide, as well as organic bases, such as collidine, lutidine, pyridine, etc. When using inorganic bases, the hydrogen chloride cleavage is suitably performed in an alcoholic solution. The reaction temperatures are preferably the boiling temperatures of the respective solvents and/or organic bases. The desired ring closure to the 1,2-methylene can also be accomplished, however, by mere filtration of the 1-chloromethyl compound, dissolved in an organic solvent, over aluminum oxide; in this process, the use of elevated temperatures becomes superfluous.

Hydrogenation of the 6-methylene compound takes place by catalytic hydrogen transfer reaction ("Kontakte" [Catalysts] [Merck] 1 (80) 3–10, which disclosure is incorporated by reference herein). By a working-up step under acidic conditions, the formulation of the 6-methyl group is enhanced. By this process, the 6-methylene compounds are valuable intermediates for preparing the 6α-methyl compounds.

Splitting off HCl for the 1,2-methylene compound and hydrogenation to obtain the 6-methyl compound can also be performed in one stage under the conditions of the catalytic hydrogen transfer reaction. According to a preferred mode of operation, the 1α-chlormethyl-6-methylene compound of Formula II is subjected to the transfer hydrogenation with cyclohexene in the presence of palladium on carbon.

The optionally following saponification of the 17α-acyloxy group is conventionally conducted with an alkali according to conventional methods.

The preparation of all of the starting compounds of Formula II can be illustrated with the aid of the reaction scheme set out below. Based thereon, all starting materials can be conventionally prepared from known starting methods or materials which are readily preparable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

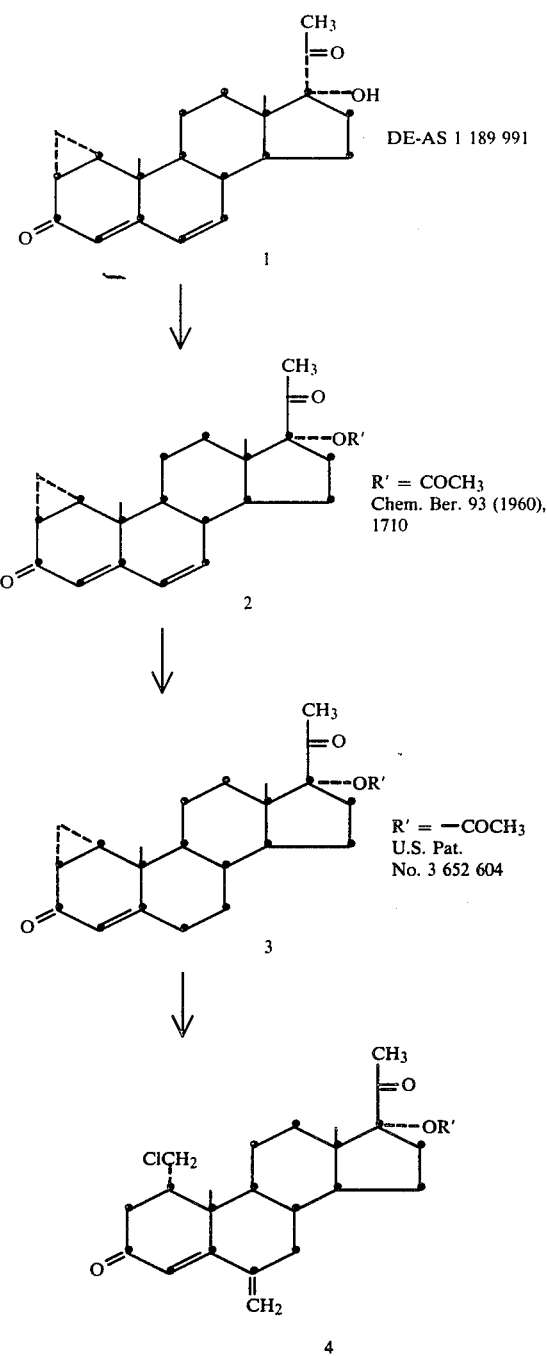

Preparation of the 17α-Acyloxy- and Methoxymethoxy-1α,2α-methylene-4,6-pregnadiene-3,20-dione (2) from the Corresponding 17α-Hydroxy Compound (1)

(a) 1α,2α-Methylene-17α-propionyloxy-4,6-pregnadiene-3,20-dione

A suspension of 7.1 g of 17α-hydroxy-1α,2α-methylene-4,6-pregnadiene-3,20-dione (DAS 1,189,991) in 114 ml of propionic acid is combined at 0° C. dropwise with 43 ml of trifluoroacetic acid anhydride. The mixture is stirred for 4 hours at room temperature and worked up as usual after precipitation into ice water-sodium chloride. The crude product is chromatographed on 600 g of silica gel with a hexane-acetone gradient (0–20% acetone), thus isolating 5.8 g of 1α,2α-methylene-17α-propionyloxy-4,6-pregnadiene-3,20-dione.

The following compounds are produced under analogous conditions:

(b) 17α-Butyryloxy-1α,2α-methylene-4,6-pregnadiene-3,20-dione (c) 1α,2α-Methylene-17α-valeryloxy-4,6-pregnadiene-3,20-dione (d) 17α-Hexanoyloxy-1α,2α-methylene-4,6-pregnadiene-3,20-dione Under nitrogen, 10.0 g of 17α-hydroxy-1α,2α-methylene-4,6-pregnadiene-3,20-dione is agitated in 200 ml of caproic anhydride with 5.0 g of p-toluenesulfonic acid for 24 hours at room temperature. The excess caproic anhydride is distilled off with steam in the presence of 50 ml of pyridine. The residue is extracted with methylene chloride, the extract is dried with sodium sulfate and concentrated under vacuum. The crude product is purified on silica gel with an acetone-pentane gradient, thus obtaining 11.3 g of 17α-hexanoyloxy-1α,2α-methylene-4,6 pregnadiene-3,20-dione. $[\alpha]_D^{25} = +85°$.

(e) 17α-Methoxymethoxy-α,2α-methylene-4,6-pregnadiene-3,20-dione

A solution of 4.0 g of 17α-hydroxy-1α,2α-methylene-4,6-pregnadiene-3,20-dione in 28 ml of anhydrous methylene chloride and 18 ml of formaldehyde dimethylacetal is combined in incremental portions with a mixture of 6.0 g of kieselguhr W 20 and 3.0 g of phosphorus pentoxide. The mixture is stirred for 45 minutes at room temperature, suctioned off, and the residue eluted repeatedly with methylene chloride. The crude product is purified on 750 g of silica gel with a hexane-acetone gradient. Yield: 3.1 g of 17α-methoxymethoxy-1α,2α-methylene-4,6-pregnadiene-3,20-dione.

Preparation of the 17α-Acyloxy- and Methoxymethoxy-1α,2α-methylene-4-pregnene-3,20-diones (3) from the Corresponding 4,6-Pregnadienes (2)

(a) 17α-Acetoxy-1α,2α-methylene-4-pregnene-3,20-dione

A solution of 60.0 g of 17α-acetoxy-1α,2α-methylene-4,6-pregnadiene-3,20-dione [R. Wiechert et al., Chem. Ber. 93: 1710 (1960)] in 1.25 l of dimethylformamide is combined with 6.3 g of 10% Pd/CaCO₃ and then hydrogenated. After a hydrogen absorption of 5.1 l, the catalyst is filtered off and the reaction solution stirred into ice water. The precipitate is suctioned off, worked up as usual, and the crude product is purified on 1.5 kg of silica gel with a pentane-acetone gradient (0–30% acetone). Yield: 34.3 g of 17α-acetoxy-1α,2α-methylene-4-pregnene-3,20-dione, mp 268°–270° C. $[\alpha]_D = +215°$.

(b) 1α,2α-Methylene-17α-propionyloxy-4-pregnene-3,20-dione

A mixture of 2 ml of cyclohexene and 5 ml of ethanol is stirred with 50 mg of 10% Pd/active carbon for one hour at a bath temperature of 80° C. After adding 500 mg of 1α,2α-methylene-17α-propionyloxy-4,6-pregnadiene-3,20-dione, the mixture is further stirred for 1.5 hours at 80° C. Subsequently the catalyst is filtered off and the filtrate concentrated to dryness under vacuum. The crude product is chromatographed on 50 g of silica gel with a hexane-acetone gradient, thus isolating 380 mg of 1α,2α-methylene-17α-propionyloxy-4-pregnene-3,20-dione.

(c) 17α-Butyryloxy-1α,2α-methylene-4-pregnene-3,20-dione

A solution of 3.0 g of 17α-butyryloxy-1α,2α-methylene-4,6-pregnadiene-3,20-dione in a mixture of 225 ml of tetrahydrofuran and 75 ml of methanol is hydrogenated with 2.7 g of tris-triphenylphosphine rhodium(I) chloride for 6.5 hours (TLC and UV control). The mixture is concentrated to dryness under vacuum, and the crude product is purified on 300 g of silica gel with a hexane-acetone gradient. Yield: 2.1 g of 17α-butyryloxy-1α,2α-methylene-4-pregnene-3,20-dione.

The following compounds are prepared from 2(c)–2(e) under hydrogenation conditions (a)–(c):

(d) 1α,2α-Methylene-17α-valeryloxy-4-pregnene-3,20-dione (e) 17α-Hexanoyloxy-1α,2α-methylene-4-pregnene-3,20-dione (f) 17α-Methoxymethoxy-1α,2α-methylene-4-pregnene-3,20-dione Preparation of the 1α-Chloromethyl-6-methylenepregnenes of General Formula II from the Corresponding 6-Desmethylene-1α,2α-methylenepregnenes (3)

(a) 17α-Acetoxy-1α-chloromethyl-6-methylene-4-pregnene-3,20-dione

A suspension of 9.0 g of sodium acetate in 270 ml of chloroform, 270 ml of formaldehyde dimethylacetal, and 35 ml of phosphorus oxychloride is stirred with 9.0 g of 17α-acetoxy-1α,2α-methylene-4-pregnene-3,20-dione for 5 hours at a bath temperature of 65° C. The reaction solution is neutralized with a saturated sodium carbonate solution and diluted with methylene chloride. The organic phase is separated and worked up as usual. The crude product is purified on 500 g of silica gel with a hexaneethyl acetate gradient (0–30% ethyl acetate), thus isolating 7.5 g of 17α-acetoxy-1α-chloromethyl-6-methylene-4-pregnene-3,20-dione, mp 190°–192° C.

The following compounds are obtained from 3(b)–3(f) under analogous reaction conditions:

(b) 1-Chloromethyl-6-methylene-17α-propionyloxy-4-pregnene-3,20-dione (c) 17α-Butyryloxy-1-chloromethyl-6-methylene-4-pregnene-3,20-dione (d) 1-Chloromethyl-6-methylene-17α-valeryloxy-4-pregnene-3,20-dione (e) 1-Chloromethyl-17α-hexanoyloxy-6-methylene-4-pregnene-3,20-dione (f) 1-Chloromethyl-17α-methoxymethoxy-6-methylene-4-pregnene-3,20-dione

EXAMPLE 1

(a) 17α-Acetoxy-1α,2α-methylene-6-methylene-4-pregnene-3,20-dione

A solution of 7.5 g of 17α-acetoxy-1-chloromethyl-6-methylene-4-pregnene-3,20-dione in 66 ml of γ-collidine is stirred for one hour at a bath temperature of 180° C. and then poured on an ice water-sodium chloride solution. The mixture is filtered off and the residue worked up as usual. The crude product is purified on 700 g of silica gel with a hexane-ethyl acetate gradient. Yield: 4.3 g of 17α-acetoxy-1α,2α-methylene-6-methylene-4 pregnene-3,20-dione, mp 205°–206° C.

Under analogous reaction conditions, the following compounds are produced from the corresponding compounds of general Formula II:

(b) 1α,2α-Methylene-6-methylene-17α-propionyloxy-4-pregnene-3,20-dione (c) 17α-Butyryloxy-1α,2α-methylene-6-methylene-4-pregnene-3,20-dione (d) 1α,2α-Methylene-6-methylene-17α-valeryloxy-4-pregnene-3,20-dione (e) 17α-Hexanoyloxy-1α,2α-methylene-6-methylene-4-pregnene-3,20-dione (f) 17α-Methoxymethoxy-1α,2α-methylene-6-methylene-4-pregnene-3,20-dione

EXAMPLE 2

17α-Hydroxy-1α,2α-methylene-6-methylene-4-pregnene-3,20-dione

Under argon, 500 mg of 17α-acetoxy 1α,2α-methylene-6-methylene-4-pregnene-3,20-dione is agitated for 16 hours in 30 ml of methanol and 16 ml of 5% sodium hydroxide solution. The mixture is poured on an ice water-sodium chloride solution and worked up as usual. The crude product is purified on 50 g of silica gel with a hexane-acetone gradient, thus isolating 380 mg of 17α-hydroxy-1α,2α-methylene-6-methylene-4-pregnene-3,20-dione.

EXAMPLE 3

(a) 17α-Acetoxy-6α-methyl-1α,2α-methylene-4-pregnene-3,20-dione

A suspension of 533 mg of 10% Pd/C in 31 ml of cyclohexene and 46 ml of ethanol is stirred for one hour at 80° C. bath temperature. To this mixture is added 7.5 g of 17-acetoxy-1-chloromethyl-6-methylene-4-pregnene-3,20-dione and the mixture is further stirred for 18 hours at 80° C. Subsequently the catalyst is suctioned off, washed with warm ethanol, and the filtrate is combined with 7 ml of concentrated hydrochloric acid. The mixture is concentrated to one-third of the reaction volume and poured on an ice water-sodium chloride solution. After the usual working-up step, the crude product is purified on 700 g of silica gel with a hexane-ethyl acetate gradient. Yield: 4.3 g of 17α-acetoxy-6α-methyl-1α,2α-methylene-4-pregnene-3,20-dione, mp 198°–200° C.

Under analogous reaction conditions, the following compounds are obtained from the corresponding compounds II:

(b) 6α-Methyl-1α,2α-methylene-17α-propionyloxy-4-pregnene-3,20-dione (c) 17α-Butyryloxy-6α-methyl-1α,2α-methylene-4-pregnene-3,20-dione (d) 6α-Methyl-1α,2α-methylene-17α-valeryloxy-4-pregnene-3,20-dione (e) 17α-Hexanoyloxy-6α-methyl-1α,2α-methylene-4-pregnene-3,20-dione (f) 17α-Methoxymethoxy-6α-methyl-1α,2α-methylene-4-pregnene-3,20-dione (g) 17α-Hydroxy-6α-methyl-1α,2α-methylene-4-pregnene-3,20-dione Under the conditions of Example 2, 450 mg of 17α-acetoxy-6α-methyl-1α,2α-methylene-4-pregnene-3,20-dione is reacted to 310 mg of 17α-hydroxy-6α-methyl-1α,2α-methylene-4-pregnene-3,20-dione, worked up, and purified. The title compound is obtained.

Examples for the Production of Topical Preparations

EXAMPLE 4

(a) Production of Oil/Water Emulsion 10.000 g of disodium edetate and 10.000 g of chlorquinaldol are dissolved in 300.000 g of purified demineralized water and combined with 10.000 g of "Carbopol".

This mixture is introduced under vigorous agitation into a melt of 80.000 g of "Vaseline"(DAB 8)—DAB being the abbreviation for the German Pharmacopoeia, official issue, 8th edition, 1978—40.000 g of stearyl alcohol, 30.000 g of "Myrj", and 50.000 g of jojoba oil. The mixture is stirred until an emulsion has been produced with a particle size of 20–70 μm.

(b) Production of Water/Oil Emulsion 230.000 g of purified demineralized water is introduced under vigorous agitation into a melt of 220.000 g of "Vaseline" (DAB 8), 10.000 g of "Dehymuls", and 10.000 g of beeswax. The mixture is stirred until an emulsion having a particle size of 20–70 μm has been formed.

(c) Preparation of a Cream

The water/oil emulsion is introduced under vigorous stirring under a vacuum of 10 torr into the oil/water emulsion. The mixture is agitated until a dispersion has been produced with a particle size of 10–50 μm, and the vacuum is removed.

Under agitation, 2.000 g of 17α-acetoxy-6α-methyl-1α2α-methylene-4-pregnene-3,20-dione—micronized; particle size predominantly 1–20 μm—is added into 98.000 g of this ointment base, and agitation is continued until the active ingredient has been uniformly distributed in the ointment base.

EXAMPLE 5

99.000 g of the ointment base prepared according to Example 4(c) is combined with 1.000 g of 17α-acetoxy-6α-methyl-1α,2α-methylene-4-pregnene-3,20-dione—micronized; particle size predominantly 1–20 μm—and agitation is continued until the active ingredient has been uniformly distributed in the ointment base.

EXAMPLE 6

Composition of an Oily Solution for the Treatment of Grave Symptoms of Androgenization 50 mg of 17α-acetoxy-6α-methyl-1α,2α-methylene-4-pregnene-3,20-dione is dissolved in
403.4 mg of castor oil and
618.6 mg of benzyl benzoate,
sterilized, and dispensed into ampoules in 1 ml portions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1α,2α-methylene-6-methylenepregnene of the formula

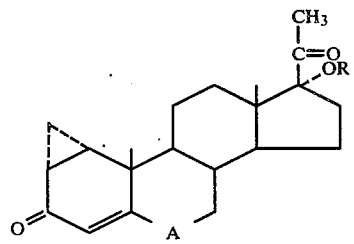

wherein
A is

and
R is hydrogen, an acyl group of a $C_{1-7}$ hydrocarbon aliphatic or aromatic carboxylic acid, or ($C_{1-3}$-alkoxy) methyl.

2. A compound of claim 1 wherein R is H.
3. 17α-Acetoxy-1α,2α-methylene-6-methylene-4-pregnene-3,20-dione,
1α,2α-methylene-6-methylene-17α-propionyloxy-4-pregnene-3,20-dione,
17α-butyryloxy-1α,2α-methylene-6-methylene-4-pregnene-3,20-dione,
1α,2α-methylene-6-methylene-17α-valeryloxy-4-pregnene-3,20-dione,
17α-hexanoyloxy-1α,2α-methylene-6-methylene-4-pregnene-3,20-dione,
17α-methoxymethoxy-1α,2α-methylene-6-methylene-4-pregnene-3,20-dione, each a compound of claim 1.
4. 17α-Hydroxy-1α,2α-methylene-6-methylene-4-pregnene-3,20-dione, a compound of claim 1.
5. A compound of claim 1, wherein R is ($C_{1-3}$-alkoxy)methyl.
6. A pharmaceutical composition comprising an antiandrogenically effective component of a compound of claim 1 and a pharmacologically acceptable carrier.
7. A pharmaceutical composition of claim 6 adapted for topical adminstration.
8. A pharmaceutical composition of claim 7 wherein the concentration of active agent is about 0.05–5% by weight.
9. A method of achieving a topical antiandrogenic effect in a patient comprising administering to the patient an amount of a 1α,2α-methylene-6-methylene- or 6α-methyl-pregnene of the formula

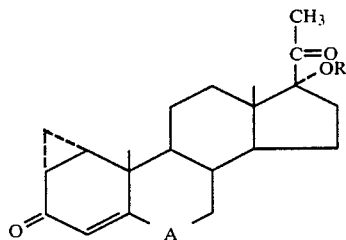

wherein
A is

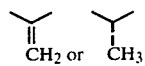

and
R is hydrogen, an acyl group of a $C_{1-7}$ hydrocarbon aliphatic or aromatic carboxylic acid, or ($C_{1-3}$-alkoxy) methyl effective as an antiandrogenic agent.
10. A method of claim 9 wherein the patient is suffering from seborrhea, acne, alopecia or hirsutism.

* * * * *